(12) United States Patent
Eddy

(10) Patent No.: US 9,717,249 B2
(45) Date of Patent: Aug. 1, 2017

(54) OFFICE FURNISHINGS HAVING AN ANTIMICROBIAL TREATMENT

(75) Inventor: Patrick E. Eddy, Allendale, MI (US)

(73) Assignee: Parasol Medical LLC, Buffalo Grove, IL (US)

( * ) Notice: Subject to any disclaimer, the term of this patent is extended or adjusted under 35 U.S.C. 154(b) by 548 days.

(21) Appl. No.: 13/448,740

(22) Filed: Apr. 17, 2012

(65) Prior Publication Data

US 2013/0273132 A1  Oct. 17, 2013

(51) Int. Cl.
| | |
|---|---|
| *A01N 25/34* | (2006.01) |
| *A01N 55/10* | (2006.01) |
| *A01P 1/00* | (2006.01) |
| *B05D 1/02* | (2006.01) |
| *B05D 1/28* | (2006.01) |
| *A01N 55/00* | (2006.01) |

(52) U.S. Cl.
CPC .................................. *A01N 55/00* (2013.01)

(58) Field of Classification Search
CPC ........ A01N 55/00; A01N 59/08; A01N 25/02; A01N 33/04; B05D 1/02; B05D 1/28
USPC ......... 424/411, 414; 427/421.1, 429; 514/63
See application file for complete search history.

(56) References Cited

U.S. PATENT DOCUMENTS

| | | | | |
|---|---|---|---|---|
| 3,654,165 | A | * | 4/1972 | Bryant ...................... 15/104.93 |
| 5,079,004 | A | | 1/1992 | Blank et al. |
| 5,428,078 | A | | 6/1995 | Cohen et al. |
| 5,959,014 | A | | 9/1999 | Liebeskind et al. |
| 6,224,579 | B1 | | 5/2001 | Modak et al. |
| 6,821,943 | B2 | | 11/2004 | Avery et al. |
| 7,045,673 | B1 | | 5/2006 | Batich et al. |
| 7,709,694 | B2 | | 5/2010 | Batich et al. |
| 7,790,217 | B2 | | 9/2010 | Toreki et al. |
| 8,025,120 | B2 | | 9/2011 | Eddy |
| 8,491,922 | B2 | | 7/2013 | Eddy |
| 2007/0042198 | A1 | | 2/2007 | Schonemyr et al. |
| 2007/0218096 | A1 | | 9/2007 | Wooley |
| 2008/0260804 | A1 | | 10/2008 | Morris et al. |
| 2010/0028462 | A1 | * | 2/2010 | Bolkan et al. ............... 424/717 |
| 2010/0167978 | A1 | * | 7/2010 | Iyer ........................ C11D 3/162 510/433 |
| 2012/0052106 | A1 | * | 3/2012 | Eddy ............................ 424/409 |
| 2012/0173274 | A1 | | 7/2012 | Rensvold et al. |

FOREIGN PATENT DOCUMENTS

WO    2008097599 A2    8/2008

OTHER PUBLICATIONS

Measurement Canada document (https://www.ic.gc.ca/eic/site/mc-mc.nsf/vwapj/VCF-FCV_CAS-67-63-0.pdf/$file/VCF-FCV_CAS-67-63-0.pdf, accessed Apr. 15, 2016, pp. 1-2).*
Murray et al., "Microbial Inhibition on Hospital Garments Treated with Dow Corning 5700 Antimicrobial Agent," Journal of Clinical Microbiology, vol. 26, No. 9, Sep. 1988, pp. 1884-1886.

* cited by examiner

*Primary Examiner* — Alma Pipic
(74) *Attorney, Agent, or Firm* — Price Heneveld LLP

(57) ABSTRACT

An office furnishing is provided that may include one or more surfaces coated with an antimicrobial treatment, which may include a silane quaternary ammonium salt and isopropyl alcohol. The silane quaternary ammonium salt may include an unreacted organofunctional silane to promote bonding to the surfaces of the office furnishing, such as 3-(trimethoxysilyl) propyldimethyloctadecyl ammonium chloride. The office furnishing article may include one of: a desk; a chair; a table; a bookcase; a hutch; shelves; an office divider panel; a file cabinet; a fax machine; a telephone; a computer; a keyboard; a monitor; a computer mouse; a book; a lamp; a binder; a stapler; an office stamp; and a desk pad. A method is also provided for coating these office furnishing articles with the antimicrobial treatment.

12 Claims, 4 Drawing Sheets

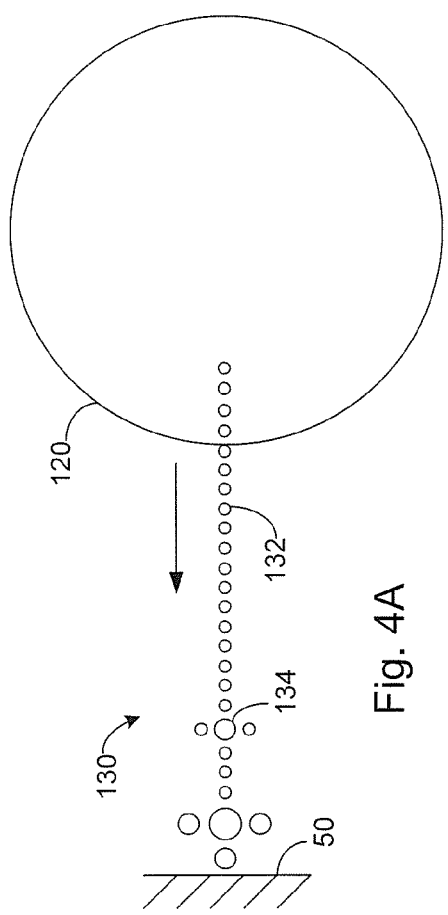
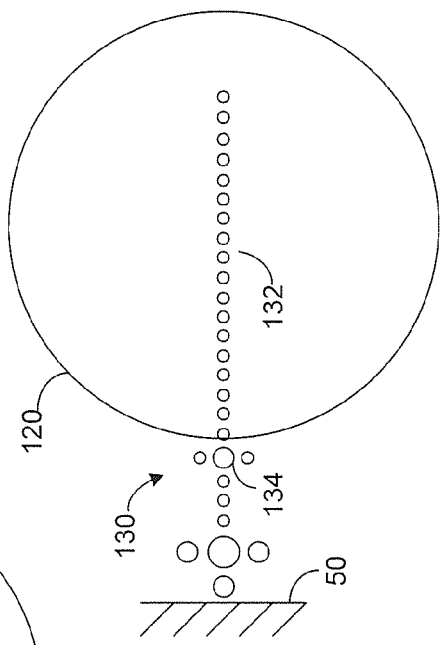
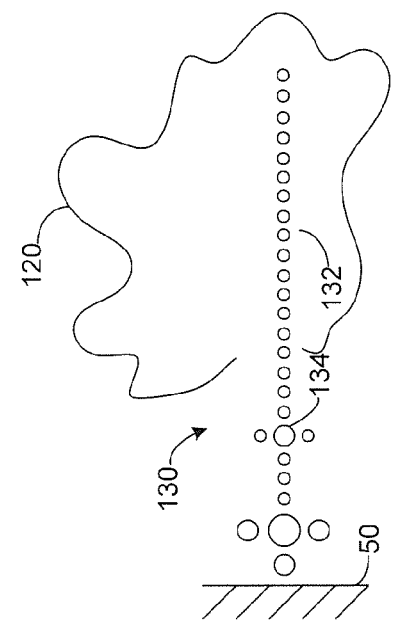
Fig. 4A
Fig. 4B
Fig. 4C

OFFICE FURNISHINGS HAVING AN ANTIMICROBIAL TREATMENT

BACKGROUND OF THE INVENTION

The present invention generally relates to office furnishings such as: a desk; a chair; a table; a bookcase; a hutch; shelves; an office divider panel; a file cabinet; a fax machine; a telephone; a computer; a keyboard; a monitor; a computer mouse; a book; a lamp; a binder; a stapler; an office stamp; and a desk pad, etc.

Hospitals continue to struggle to prevent dangerous infections caused by bacteria such as MRSA, and others. Although hospital staff wipes down parts of the hospital rooms with disinfectants, the dangerous bacteria remain present in hospitals. Areas that are sometimes overlooked in a hospital are furnishings within offices, as well as reception and waiting areas.

Even offices outside of a hospital or healthcare facility are prone to harbor bacteria and therefore would benefit from being disinfected. Most common disinfectants, however, only kill bacteria present on an article at the time the disinfectant is applied, and thus such treatment is ineffective in preventing bacteria from subsequently collecting on the article.

SUMMARY OF THE INVENTION

According to an embodiment of the present invention, an office furnishing is provided comprising an office furnishing article comprising a plurality of surfaces, wherein at least one of the surfaces is coated with an antimicrobial treatment, wherein the antimicrobial treatment comprises a silane quaternary ammonium salt, wherein the office furnishing article comprises one of: a desk; a chair; a table; a bookcase; a hutch; shelves; an office divider panel; a file cabinet; a fax machine; a telephone; a computer; a keyboard; a monitor; a computer mouse; a book; a lamp; a binder; a stapler; an office stamp; and a desk pad.

According to another embodiment of the present invention, a method is provided for treating an office furnishing with an antimicrobial treatment solution comprising the steps of: providing an antimicrobial treatment solution comprising isopropyl alcohol and an antimicrobial treatment substance, wherein the antimicrobial treatment substance comprises a silane quaternary ammonium salt; and applying the antimicrobial treatment solution to at least one surface of the office furnishing.

In one or more of these embodiments, the silane quaternary ammonium salt may have an unreacted organofunctional silane to promote bonding to the surfaces of the office furnishing. The silane quaternary ammonium salt may comprise 3-(trimethoxysilyl) propyldimethyloctadecyl ammonium chloride.

These and other features, advantages, and objects of the present invention will be further understood and appreciated by those skilled in the art by reference to the following specification, claims, and appended drawings.

BRIEF DESCRIPTION OF THE DRAWINGS

In the drawings:

FIG. 4A is a schematic representation of the monomer shown in FIGS. 2 and 3 illustrating a first step in the manner by which the monomer destroys a microbe;

FIG. 4B is a schematic representation of the monomer shown in FIGS. 2 and 3 illustrating a second step in the manner by which the monomer destroys a microbe; and FIG. 4C is a schematic representation of the monomer shown in FIGS. 2 and 3 illustrating a third step in the manner by which the monomer destroys a microbe.

DETAILED DESCRIPTION OF PREFERRED EMBODIMENTS

Figure 1:
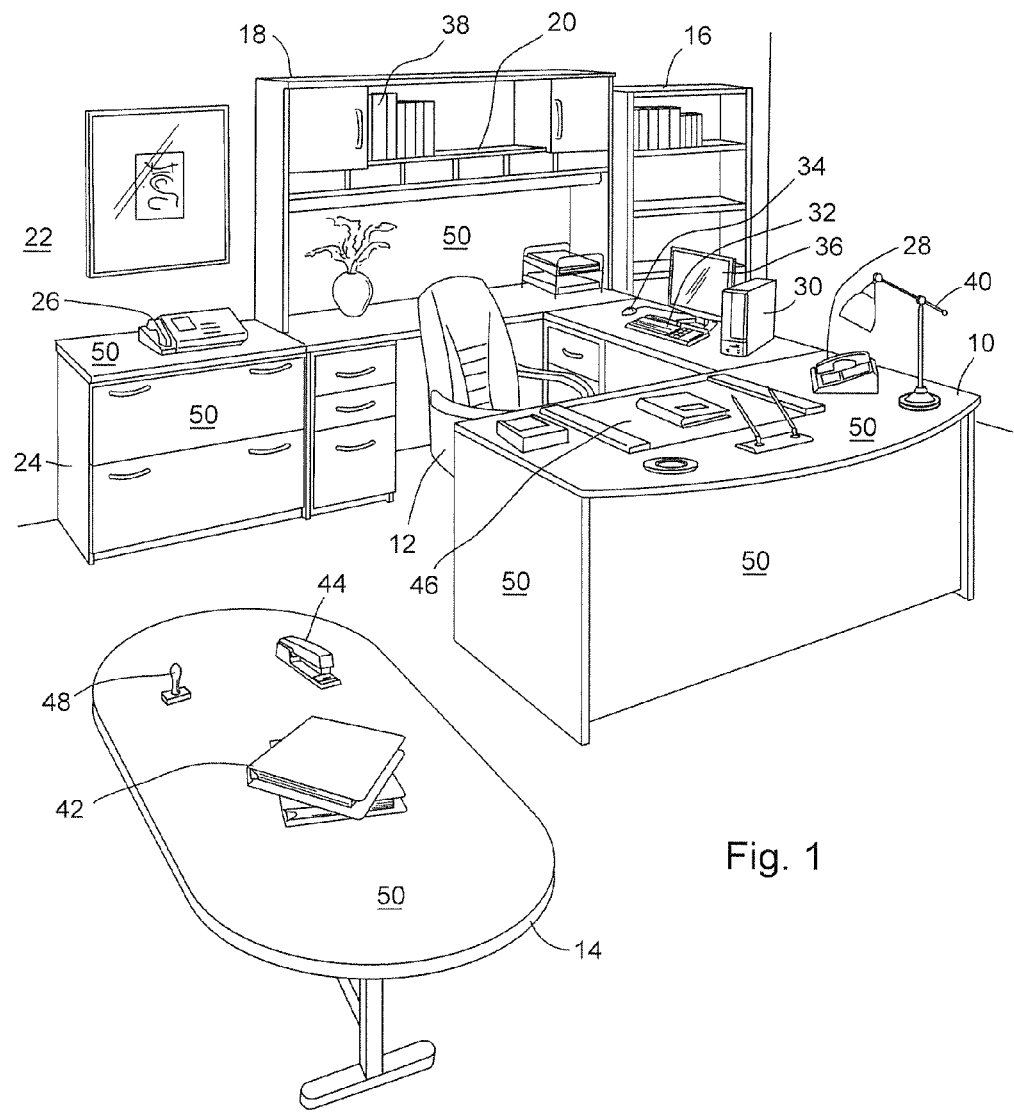
FIG. 1 is a perspective view of an office including various furnishings treated in accordance with an embodiment of the present invention.

Reference will now be made in detail to the present preferred embodiments of the invention, examples of which are illustrated in the accompanying drawings. Wherever possible, the same reference numerals will be used throughout the drawings to refer to the same or like parts. In the drawings, the depicted structural elements are not to scale and certain components are enlarged relative to the other components for purposes of emphasis and understanding.

FIG. 1 shows an example of an office containing various office furnishings that may have one or more of their surfaces coated with an antimicrobial treatment. As illustrated, such office furnishings may include any one or more of the following articles: a desk 10; a chair 12; a table 14; a bookcase 16; a hutch 18; a shelf 20; an office divider panel 22; a file cabinet 24; a fax machine 26; a telephone 28; a computer 30; a keyboard 32; a computer mouse 34; a monitor 36; a book 38; a lamp 40; a binder 42; a stapler 44; a desk pad 46; and an office stamp 48 for marking materials such as faxed, copy, paid, rush, draft, confidential etc. Note that desk 10 may be a reception desk and chair 12 may one of several chairs in a waiting room, conference room, or lobby.

In general, the antimicrobial treatment may be applied to all surfaces of the above office furnishing articles. However, bottom surfaces or surfaces against a wall or other article that typically do not come into contact with people may not need to be treated. Surfaces that regularly come into contact with people are surfaces best treated with the antimicrobial treatment.

The components of the office furnishings are often constructed of a variety of materials including wood, fabrics, vinyls, metals, laminates and a variety of plastics. Each of these components has outer surfaces 50, which are coated with the antimicrobial treatment as described further below. Preferably all surfaces 50 of the components of the office furnishing articles are treated.

The surfaces 50 of the articles are coated with an antimicrobial treatment that may be sprayed onto the surfaces using a solution and/or may be applied using wipes soaked in such a solution. Suitable wipes and solutions are disclosed in commonly-assigned U.S. patent application Ser. No. 13/182,657, entitled "ANTIMICROBIAL WIPES AND SOLUTION," filed on Jul. 14, 2011, by Patrick E. Eddy, now U.S. Pat. No. 8,491,922, the entire disclosure of which is incorporated herein by reference.

In a preferred form, the antimicrobial treatment solution contains 30-50 percent isopropyl alcohol and 50-70 percent antimicrobial treatment substance, which is preferably a silane quaternary ammonium salt having an unreacted organofunctional silane. If the antimicrobial treatment solution is applied by spraying, the solution most preferably includes 50 percent isopropyl alcohol and 50 percent of the unreacted antimicrobial treatment substance. If the solution is applied using the wipes, the solution is preferably 30 percent isopropyl alcohol and 70 percent of the unreacted antimicrobial treatment substance.

The preferred silane quaternary ammonium salt includes an active ingredient of 3-(trimethoxysilyl) propyldimethyloctadecyl ammonium chloride and other inert ingredients. The silane quaternary ammonium salt preferably includes about 3.6 percent of the 3-(trimethoxysilyl) propyldimethyloctadecyl ammonium chloride. Such a silane quaternary ammonium salt is available from Aegis Environments, of Midland, Mich., and is identified as "AEM 5772-5 Antimicrobial." The antimicrobial treatment solution with the isopropyl alcohol is available from MicrobeCare, LLC of Allendale, Mich., under the trademark MICROBECARE™.

The isopropyl alcohol may have a concentration of 70-90 percent. By providing the unreacted organofunctional silane in isopropyl alcohol, the organofunctional silane does not react with the wipe substrates or the inside of the wipe container such that it is free to later react and permanently covalently bond with the surfaces 50 of the office furnishing article. Isopropyl alcohol is preferred as it evaporates quickly once the solution is wiped onto the treated surface to allow the unreacted organofunctional silane to more quickly react with the treated surface.

The above described silane quaternary ammonium salt is preferred because it is an organofunctional silane antimicrobial treatment substance that is substantially free from arsenic, silver, tin, heavy metals and polychlorinated phenols; copper; or a silver-ion emitter. In addition, it not only eliminates bacteria on contact, but it remains on the treated surfaces 50 and kills any bacteria subsequently contacting these surfaces. Such treatment preferably lasts at least one week, more preferably several months, and most preferably indefinitely.

Figure 2:
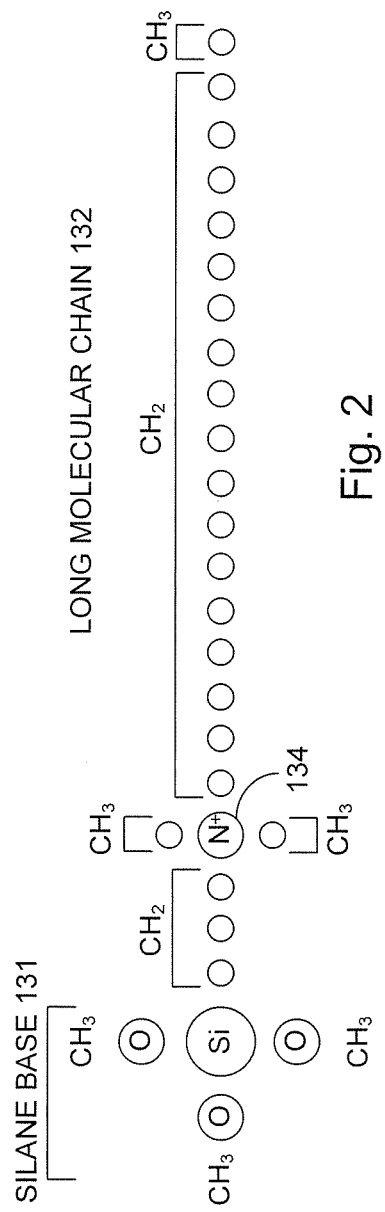
FIG. 2 is a schematic representation of a monomer that may be used in the embodiments described herein as an antimicrobial treatment substance.
Figure 3:
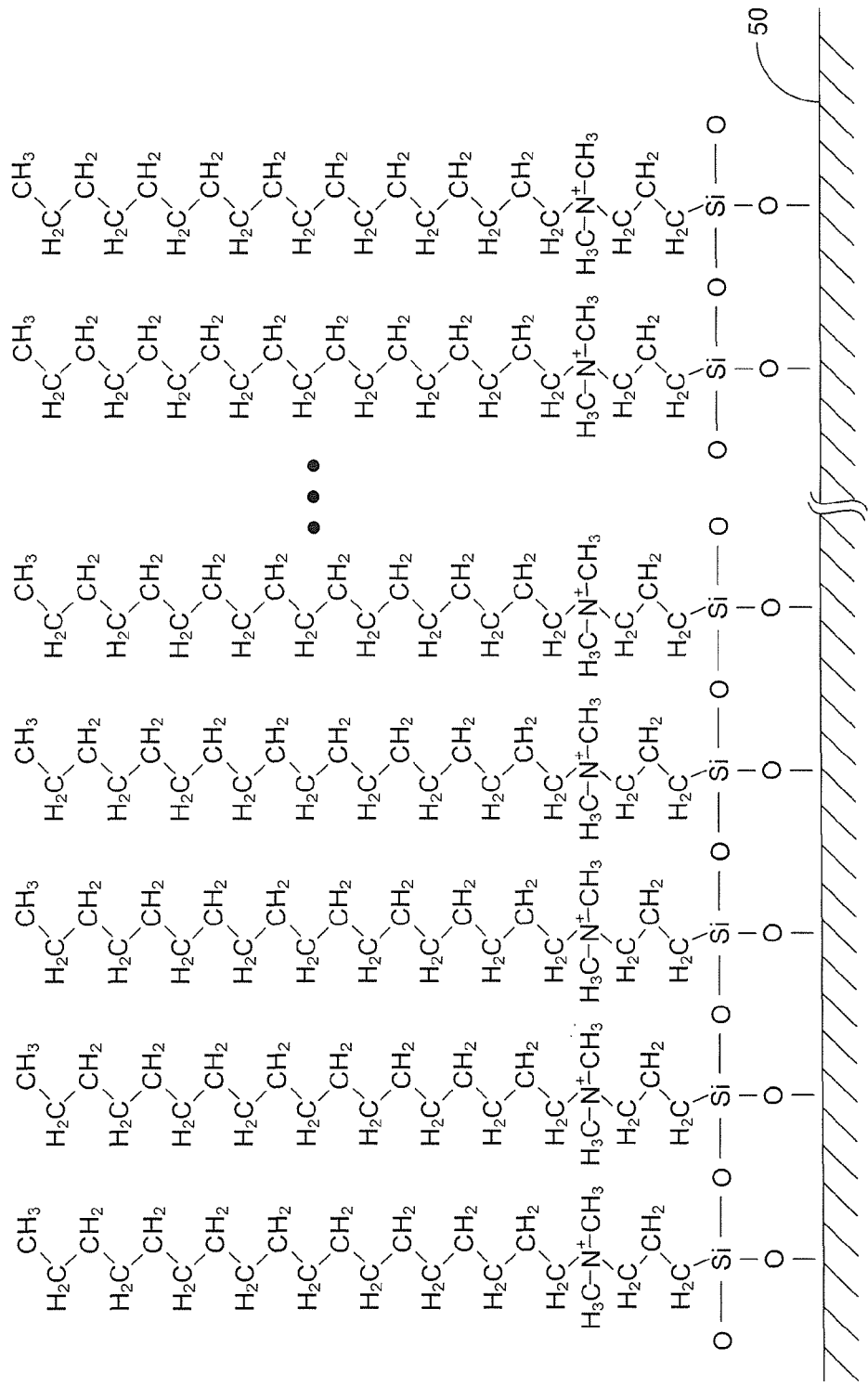
FIG. 3 is a schematic representation of a plurality of the monomers shown in FIG. 2 as applied to a treated surface.

FIG. 2 shows a schematic representation of a monomer form 130 of a preferred organofunctional silane serving as the antimicrobial treatment substance. As illustrated, monomer 130 includes a silane base 131 for bonding to a surface 50, a positively charged nitrogen molecule 134, and a long molecular chain 132. As shown in FIG. 3, the silane bases of these monomers covalently and permanently bond to each other and to the surface 50 to be treated in such a way that the long molecular chains are aligned and pointing outward from the surface 50. This tight bonding provides a micropolymer network that serves as a protective coating on the outside of the surface 50 that destroys any microbes that come into contact.

The manner by which the preferred organofunctional silane destroys microbes is illustrated in FIGS. 4A-4C. Such microbes may include bacteria, mold, mildew, algae, etc. As shown in FIG. 4A, the cell membrane 120 of the microbe is attracted to the treated surface 50 of the office furnishing and then is punctured by the long molecular chain 132 of the monomer 130. As the microbe is drawn closer because of the positive-negative ion exchange, the monomer 130 penetrates further into the cell membrane 120 as shown in FIG. 4B. Once the cell membrane 120 is penetrated deeply, it is physically ruptured by a sword-like action and then electrocuted by a positively charged nitrogen molecule 134 of the monomer 130, thus destroying the microbe as illustrated in FIG. 4C. Thus, the microbes are eliminated without "using up" any of the antimicrobial active ingredients, which remain on the surfaces 50 ready to continue protecting the treated item against further microbial contamination.

The preferred organofunctional silane also prevents odor, staining and product deterioration that may be associated with microbe contamination. The preferred organofunctional silane is also beneficial because it permanently bonds to a treated surface, covers a broad spectrum of activity with no negative effects or drawbacks, and is easily incorporated and easily verifiable.

The preferred organofunctional silane is designed to react and create a covalent bond with the surfaces 50 of the office furnishing article. The reacted substance is held onto those surfaces 50 until the covalent bond is broken. Tests have shown that most industrial cleaners or disinfectants will not remove the preferred antimicrobial treatment substance. The method of removal is by abrasion.

The above description is considered that of the preferred embodiments only. Modifications of the invention will occur to those skilled in the art and to those who make or use the invention. Therefore, it is understood that the embodiments shown in the drawings and described above are merely for illustrative purposes and not intended to limit the scope of the invention, which is defined by the claims as interpreted according to the principles of patent law, including the doctrine of equivalents.

I claim:

1. An office furnishing comprising:
   an office furnishing article comprising a plurality of surfaces, wherein at least one of said plurality of surfaces comprises a coating of an antimicrobial treatment solution,
   wherein the office furnishing article comprises one of: a desk; a chair; a table; a bookcase; a hutch; shelves; an office divider panel; a file cabinet; a computer; a keyboard; a monitor; a computer mouse; a book; a lamp; a binder; a stapler; an office stamp; and a desk pad,
   and wherein said antimicrobial treatment solution consists of isopropyl alcohol and a silane quaternary ammonium salt.

2. The office furnishing of claim 1, wherein said silane quaternary ammonium salt includes an unreacted organofunctional silane capable of bonding to the at least one of said plurality of surfaces of the office furnishing article.

3. The office furnishing of claim 1, wherein the silane quaternary ammonium salt is covalently bonded to the at least one of said plurality of surfaces and is capable of emitting ions that aid in destruction of a microbe.

4. The office furnishing of claim 1, wherein said office furnishing is a desk, wherein at least a top surface of the desk comprises a coating of the antimicrobial treatment solution.

5. The office furnishing of claim 1, wherein said office furnishing is a table, wherein at least a top surface of the table comprises a coating of the antimicrobial treatment solution.

6. The office furnishing of claim 1, wherein said office furnishing is a chair, wherein at least a seat bottom of the chair and a seat back of the chair comprise a coating of the antimicrobial treatment solution.

7. The office furnishing of claim 1, wherein said office furnishing is a file cabinet, wherein at least a drawer handle surface of the file cabinet comprises a coating of the antimicrobial treatment solution.

8. A method for treating an office furnishing with an antimicrobial treatment solution comprising the steps of:

providing an antimicrobial treatment solution consisting of isopropyl alcohol and a silane quaternary ammonium salt; and applying the antimicrobial treatment solution to at least one surface of the office furnishing, wherein upon applying the antimicrobial treatment solution, an antimicrobial coating is formed on the at least one surface of the office furnishing by forming covalent bonds between the antimicrobial treatment solution and the at least one surface of the office furnishing.

9. The method of claim 8, wherein the silane quaternary ammonium salt includes an unreacted organofunctional silane capable of bonding to the at least one surface of the office furnishing.

10. The method of claim 8, wherein the step of applying the antimicrobial treatment solution to the at least one surface of the office furnishing includes spraying the antimicrobial treatment solution onto the at least one surface of the office furnishing.

11. The method of claim 8, wherein the step of applying the antimicrobial treatment solution to the at least one surface of the office furnishing includes providing a wipe soaked in the antimicrobial treatment solution and wiping the at least one surface of the office furnishing with the wipe soaked in the antimicrobial treatment solution to transfer the antimicrobial treatment solution to the at least one surface of the office furnishing.

12. An office furnishing comprising:

an office furnishing article comprising a plurality of surfaces, wherein at least one of said plurality of surfaces comprises a coating of an antimicrobial treatment solution, wherein the office furnishing article comprises one of: a bookcase; a hutch; shelves; an office divider panel; a computer; a keyboard; a monitor; a computer mouse; a book; a lamp; a binder; a stapler; an office stamp; and a desk pad, wherein the antimicrobial treatment solution is covalently bonded to the at least one of said plurality of surfaces and is capable of emitting ions that aid in destruction of a microbe, and wherein said antimicrobial treatment solution consists of isopropyl alcohol and a silane quaternary ammonium salt.

* * * * *